United States Patent [19]
Roth

[11] 3,937,223
[45] Feb. 10, 1976

[54] COMPACTED SURGICAL HEMOSTATIC FELT

[75] Inventor: Roy William Roth, New Canaan, Conn.

[73] Assignee: American Cyanamid Company, Stamford, Conn.

[22] Filed: Apr. 19, 1974

[21] Appl. No.: 462,559

[52] U.S. Cl. ............... 128/325; 128/156; 128/296; 128/334 R
[51] Int. Cl.² ........................................ A61L 15/04
[58] Field of Search............ 128/334 R, 335, 335.5, 128/156, 296

[56] References Cited
UNITED STATES PATENTS

| | | | |
|---|---|---|---|
| 2,896,618 | 7/1959 | Schaefer | 128/296 X |
| 3,122,479 | 2/1964 | Smith | 128/325 X |
| 3,542,634 | 11/1970 | Such et al. | 128/156 X |
| 3,545,442 | 12/1970 | Wicker et al. | 128/156 X |
| 3,666,750 | 5/1972 | Briskin et al. | 128/325 X |
| 3,739,773 | 6/1973 | Schmitt et al. | 128/334 R X |
| 3,797,499 | 3/1974 | Schneider | 128/334 R |

*Primary Examiner*—Dalton L. Truluck
*Attorney, Agent, or Firm*—Samuel Branch Walker

[57] ABSTRACT

Tissue absorbable synthetic polymeric fibers, such as polyglycolic acid, are felted to form a thin mat with at least one, and preferably both, surfaces compacted by contact with a heated embossing surface such as a hot roller. Porosity is reduced but the compacted felt retains its flexibility, and conforms readily to the surface of a bleeding wound to give effective rapid hemostasis. The hemostatic felt is conveniently but not necessarily allowed to remain in place during the healing process and is absorbed by living tissue.

8 Claims, 9 Drawing Figures

3 mm 3 mm

.3 mm

.3 mm 0.3 mm 0.3 mm

COMPACTED SURGICAL HEMOSTATIC FELT

BACKGROUND OF THE INVENTION

The problem of bleeding has caused complications in surgery or after traumatic damage for generations. Different techniques have been used to control the flow of blood, such as the application of hot tar during a more barbaric age, or the use of sutures or ligatures to tie off bleeding vessels or a small cautery being used to burn bleeders, or assorted clamps, adapted for particular surgical techniques. Various forms of dressings have been used to encourage clotting or otherwise control the flow of blood. Various forms of absorbable elements for contact with the wound surface have been suggested, including such materials as foamed gelatin or knitted oxidized regenerated cellulose. The history of surgery shows many other materials have been used to control bleeding.

In general, the desirable aspects of hemostats are recognized, but new and improved hemostats are in demand.

DESCRIPTION OF THE PRIOR ART

Uses of polyglycolic acid are disclosed in a series of patents and applications to Schmitt, et al:

U.S. Pat. No. 3,297,033, Schmitt and Polistina, Jan. 10, 1967, SURGICAL SUTURES, discloses polyhydroxyacetic ester absorbable sutures. The material is also called polyglycolic acid, and is disclosed as permitting small quantities of comonomers to be present, such as dl-lactic acid, its optically active forms, homologs and analogs. A small quantity is recognized by the art as up to 15%, as shown by U.S. Pat. No. 2,668,162, Lowe, Feb. 2, 1954, PREPARATION OF HIGH MOLECULAR WEIGHT POLYHYDROXY-ACETIC ESTER.

U.S. Pat. No. 3,463,158, Schmitt and Polistina, Aug. 26, 1969, POLYGLYCOLIC ACID PROSTHETIC DEVICES, discloses surgical uses of polyglycolic acid, and incorporates definitions of some terms.

U.S. Pat. No. 3,620,218, Schmitt and Polistina, Nov. 16, 1971, CYLINDRICAL PROSTHETIC DEVICES OF POLYGLYCOLIC ACID, lists many uses of polyglycolic acid.

U.S. Pat. No. 3,736,646, Schmitt and Epstein, June 5, 1973, METHOD OF ATTACHING SURGICAL NEEDLES TO MULTIFILAMENT POLYGLYCOLIC ACID ABSORBABLE SUTURES, discloses surgical elements of a copolymer containing from 15 to 85 mol percent glycolic acid and 85 to 15 mol percent lactic acid.

U.S. Pat. No. 3,739,773, Schmitt and Polistina, June 19, 1973, POLYGLYCOLIC ACID PROSTHETIC DEVICES, claims particularly bone pins, plates, nails and screws of polyglycolic acid.

U.S. application Ser. No. 365,656, now U.S. Pat. No. 3,875,937, Schmitt and Polistina, May 31, 1973, SURGICAL DRESSINGS OF ABSORBABLE POLYMERS, discloses additional subject matter on surgical dressings of polyglycolic acid.

U.S. Pat. No. 3,739,773, supra, lists a number of U.S. patents on methods for preparing polyglycolic acid and starting materials therefor.

In U.S. Pat. No. 3,620,218, supra, in Column 2 are listed a number of medical uses of polyglycolic acids, including in Column 2; line 52, knitted or woven fibrillar products, including velours, and mentioning specifically in line 53, burn dressings; line 57, felt or sponge for liver hemostasis; line 63, foam as an absorbable prosthesis; and in lines 74 and 75, burn dressings (in combination with other polymeric films).

U.S. Pat. No. 3,783,093, Gallacher, Jan. 1, 1974, FIBROUS POLYETHYLENE MATERIALS, discloses a fibrillated material, mentioning poly(glycolic acid) among others, in which one resin is mixed and fibrillated with another, and one leached out to give the product, a web of oriented, interconnected directional fiber-like strands, membranes, ribbons, branched ribbons and fibrils. These can be used as bandages and for other medical purposes. Example 15 shows 25 parts of poly(glycolic acid) and 75 parts of poly-(methyl methacrylate) leached with acetone.

The use of gauzes, felts, and knitted fabrics as a wound dressing is quite conventional. The use of collagenous products as a sponge or pad has been disclosed.

Commercially, an oxidized regenerated cellulose is available as a hemostat. Also, a gelatin foam product is distributed in sheet form. Both of these are absorbable in tissues. Under some conditions, the gelatin foam causes bile cysts. It is desirably wetted with saline at the time of use and to wet with saline, squeeze out, rewet and squeeze out again is time consuming, and renders the material limp and somewhat pasty so that it may stick to instruments and gloved fingers. In addition, on contact with blood the foam gelatin has a tendency to swell and unduly increase its bulk. Suction cannot be applied through the foam. The oxidized cellulose may acquire a gelatinous consistency and stick to gloves and instruments. As it is knitted, when cut, flakes of the material may scatter.

The complete disclosures of the above patents and articles are hereby herein incorporated by this reference thereto.

It is quite common for persons who have cut themselves while shaving to stop bleeding by placing a small piece of toilet tissue on the wound. If the cut is small, the tissue adheres to the skin, and bleeding stops. The tissue is trapped in the scab, and is later removed — sometimes bleeding resumes. Often the tissue floats on accumulating and other measures are required to stop the bleeding.

SUMMARY OF THE INVENTION

This invention relates to a tissue absorbable synthetic polymeric fiber felt hemostat which is heat compacted on at least one surface. The compaction and heat embossing aid is causing the hemostatic surgical felt to adhere to the surface of a wound, and because it adheres so closely due to capillarity, hemorrhage is usually effectively controlled. If a major blood vessel is severed, the hemostatic felt may be floated from the surface of a wound, but for many procedures, such as the excision of a part of a liver or neurosurgery, the adherence is such as to promptly cause hemostasis. The compacted hemostatic felt is preferably thick enough and compacted enough that blood does not flow from the outer surface; and because of the absorbable characteristic of the felt, the hemostatic felt may be left in place when a wound is closed, to give effective blood flow control during the surgical procedure, minimize subsequent bleeding and be readily absorbable by living tissue so there is no need to remove the hemostat, which might cause renewed bleeding.

The hemostatic felt is produced by the random formation, as, for example, by air-scattering, of a felt followed by heat embossing. Conveniently, the fibers are within the range of 0.5 to 12 denier and a length of at least ¼ inch continuous fibers may be used, but chopping into a length of ¼ inch to 2 or 3 inches makes handling and air laying as a felt more convenient. The air laid web may then be felted, in accordance with conventional procedures, either using a nonoriented rubbing or a needling in which barbed needles cause interlocking of the polyglycolic acid fibers. If embossed, mechanical felting may be used but is not required.

Even if the laying or felting process introduces some orientation, the compaction of the felt gives enough strength in all directions so that the compacted felt forms a good hemostat.

Whereas an ordinary felt, such as disclosed in U.S. Pat. No. 3,620,218, supra, gives at least some hemostasis, uncompacted felted fibers give a felt which may float from a bleeding surface, and is too porous. The normal texture of the felt surface tends to be held from the wound surface by the random orientation and soft surface of the conventional felted surface.

It has now been found that embossing and compacting the fibers on the tissue contacting surface aids in causing the felt to adhere sufficiently closely to hold the felt to the wound, and compacting the free surfaces reduces the tendency for blood to flow through the felt. The felt is thinner, which reduces the blood volume in the hemostat, so that absorption during healing is more rapid. The absorbable felt fibers, such as polyglycolic acid absorb readily during the healing process, but massive residual blood clots can be more of a problem. It is desirable that a minimum of pooled blood or blood clots be formed in the wound so that absorption of the clotted blood is more rapid.

The fibers themselves are absorbable by living tissue so that any of the fibers within the wound are absorbed by the living tissue without deleterious effects.

The present compacted absorbable felt may be used on almost any type of wound in which the skin is broken and body fluids, particularly blood and serum, are released by the wound. It is primarily designed for use as a hemostat on any bleeding surface, and is particularly adapted to procedures in which the compacted felt hemostat is closed into a wound, to be absorbed by living tissue as the wound heals. It is also very effective on skin surface wounds, in which the compacted felt hemostat is on the skin surface, and at least part of the felt may be trapped within the wound. It may be used to wipe liquids from tissue surfaces as a sponge, with the advantage any fibers shed into and trapped within the wound are absorbed, and hence are innocuous.

For adequate conformation, the compacted felt must be flexible so that it can conform to the topography of the wound and at the same time it must be sufficiently flexible that as the tissues move, the compacted felt can move with them. Usually, as a hemostat, the blood coagulates and may harden within the felt structure, and the characteristics of the clotted blood determine the flexibility of the healing structure.

The tissue absorbable fibers which may be used to provide the hemostatic surgical felt include those fibers which are reasonably rapidly absorbed in tissue, that is, within a period of less than about 90 days. Polymers in which tissue absorption results from the hydrolytic degradation of glycolic acid ester linkages give good results. Because strength of the fibers is not a major requirement, a copolymer containing considerable lactic acid makes a good hemostat. Such polymers are disclosed in U.S. Pat. No. 3,736,646, supra.

A polymer having an ordered configuration of glycolic units and lactic acid units which is tissue absorbable is described at length of Ser. No. 435,365, Jan. 24, 1974, Augurt, Rosensaft and Perciaccante, UNSYMMETRICALLY SUBSTITUTED 1,4-DIOXANES 2,5-DIONES.

Another absorbable polymer which may be used for the hemostat is poly(N-acetyl-D-glucosamine), such as described in U.S. Ser. No. 441,717, Feb. 11, 1974, Richard Carl Capozza, POLY(N-ACETYL-D-GLUCOSAMINE) PRODUCTS.

A preferred tissue absorbable fiber is made from homopolymeric polyglycolic acid, which among other polymers is described in the Schmitt patents above, and which is meeting with commercial success as a suture. Because this material is in current use as a suture, has been approved by governmental authorities, and is recognized as usable by the medical profession, most of the examples and description will be in connection with such a fiber; although it is to be understood that other tissue absorbable fibers may be used.

Because the felt is normally under a minimal load, a form of polyglycolic acid which is weaker than desirable for sutures is perfectly satisfactory in a hemostatic felt and additionally because the major requirements for hemostatic action are during the course of an operation, a form of PGA which loses its strength within 24 hours or less gives good results as a hemostat and is rapidly absorbed by tissues during the healing process. Once bleeding has been completely controlled and the wound closed, the likelihood of subsequent bleeding is markedly reduced and after a period of only a few days the healing process is sufficiently advanced that hemorrhage is not a problem. It is desirable that strength be retained for at least a few days to leave a margin for safety and some protection for the wound surface during a considerable portion of the healing process. Because of variations within species and because of variations in individual members of a species and variations in tissue characteristics of the site of use at which hemorrhage is controlled, minimum and maximum absorption times can vary considerably. To be on the safe side, it is desirable that the hemostatic felt be well within an acceptable range. A material that retains a considerable portion of its strength for at least three days and is substantially completely absorbed within 90 days gives highly advantageous results.

It is important that the tissue absorbable polymer be of a material that is not deleterious to living human tissue and that it be spinnable as a fiber which forms a fine structure such that blood and other fluids wet but do not flow rapidly therethrough. It needs sufficient strength to maintain its integrity as a hemostatic sponge during manufacturing and use. It should be absorbed before it can act as a foreign body after the wound has healed.

The above two patent applications, disclosures of which are herein incorporated by this reference thereto, are examples of such materials. Inasmuch as the useful characteristics of the present compacted felt are largely a function of the size, shape and structure, other tissue absorbable materials may be substituted for the homopolymeric polyglycolic acid fibers described in more detail in the following examples.

Polyglycolic acid fibers and their manufacture are described in the patents listed above, particularly the list set forth in U.S. Pat. No. 3,739,773, supra.

Polyglycolic acid is conveniently spun into the filaments of about 0.5 to 12 deniers per filament. Smaller filaments are quite difficult to spin and larger ones are stiffer than is desirable although there are many uses for which both larger and smaller are acceptable. Conveniently, from about 2 to 6 deniers per filament gives a good compromise between ease of spinning and sufficient flexibility to form a good felt and is preferred. Conveniently, but not necessarily, a group of fibers are spun together as a tow. The tow may be twisted, or at least false twisted, and heat treated to give a crimped and textured configuration to the yarn after which it is preferably chopped into segments of about ½ inch to about 3 inches using conventional cutting techniques to give a staple. It may be used straight — that is, without crimping.

Other conventional methods of crimping may be used, such as a stuffer box, a knit-deknit process, or crimping gears, or a bicomponent fiber, in which different molecular weights of polymer are used as components. An uncrimpted fiber gives good results if needle punched, a conventional felting technique. The cut fibers are sprinkled or air laid into a web having a density of from about 0.5 ounces per square yard to about 4 ounces per square yard. The densities above about 1.5 ounces per square yard are more effective hemostats over a wider range of surgical procedures than are the lighter webs. The webs may be felted by the usual rubbing or needling techniques to give a three dimensional configuration with interlocked fibers which gives strength to the felt. It may be only heat embossed to give adequate strength.

The felt is embossed, preferably on both sides, to give a less porous felt and one in which the surface fibers are pressed down into the structure. By having the surface fibers pressed into the structure so that a smoother surface is obtained, the embossed felt when placed in contact with a wound surface can be drawn into closer conformity with the wound and reduce pockets in which blood or other fluids can accumulate, and by being drawn against the wound by capillarity, the embossed hemostatic felt is held closely enough to the wound surface that it is drawn to the wound surface and does not float off.

The embossing may be accomplished conveniently by using a hot embossing roll which without melting the fibers gives them a permanent press and smooth flat surface. At faster speeds, a higher temperature can conveniently be used on the embossing roll. Good results are obtained using a roll temperature of 350°F., a pressure of about 1050 pounds per linear inch of contact of rolls and a feed rate of 15 feet per minute. A stainless steel heated embossing roll is used against a nylon backing roll.

Embossing on the tissue contacting surface gives improved adherence to the tissues and increases the effective surface area exposed to blood. Blood can ooze through the hemostatic embossed felt and pool on the free surface. If the free surface is also embossed, it gives a local increased compactness which aids in preventing blood from oozing through the free surface so that only the felt thickness between the two embossed surfaces is filled with blood. By having a minimum thickness of felt filled with blood, the later absorption of the blood clot is expedited. The tissue absorbable material, such as homopolymeric polyglycolic acid is absorbed at such a rate that its presence in the wound presents no complications. A major blood clot may cause scar formation or delayed absorption.

Although not limited thereto, it is convenient to make the present felt from fibers such as are used for sutures. The breaking strength of such fibers varies from around 20,000 pounds per square inch to over 100,000 pounds per square inch. A weaker fiber is adequate for felts used as hemostats.

The felts used as hemostats themselves are conveniently formed by needling uncrimped fibers such as are used in sutures, but the felt may be embossed without needling.

The stiffness of the felt may be determined by standard methods such as set forth in Federal Test Method Standard 191 of Dec. 31, 1968, Method 5206. In this method a test specimen of rectangular cloth 6 inches long and 1 inch wide is placed on a horizontal platform and slid off under test conditions until the end of the fabric drops to an angle of 41½° below the plane of the surface of the platform. The material is tested under standard conditions as set forth in the Federal Test Method Standard 191. Other test procedures may be used but the increase in relative stiffness of the embossed felt over the unembossed felt is one characteristic of a satisfactorily embossed felt hemostat.

If the felt is not needled, but merely the air laid web is used, it is somewhat more flexible than if needled but after embossing under heat using either a diamond or a burlap embossing roll, the felt is compressed and is a satisfactory hemostat.

Another measure of the effect of the heat embossing is the air permeability. The air permeability is conveniently measured by the standard method of test for air permeability of textile fabrics, ASTM Standards Designation D 737-69 (Oct. 3, 1969). In this method under standard conditions, air at a pressure of 0.5 inches of water is flowed through an orifice over which the fabric is finely spread, usually having a diameter of 2.75 inches, and the rate of air flow is expressed conveniently in cubic feet of air per minute per square foot of fabric at the pressure differential of 0.5 inch of water. A Gurley Permeometer is one satisfactory device for this test method, and uses a guard ring to avoid leakage through the edges of the fabric. As shown below, the heat embossed fabric has a markedly lower air permeability than the felt before the heat embossing.

Conveniently, but not necessarily, the embossing roll has a plurality of small diamond-shaped engravings therein so that the fabric is embossed with a series of lines dividing the felt surface into diamond-shaped raised portions.

Another good embossing roll has a configuration of the surface approximately that of burlap so that the finished felt has a general configuration of burlap. Other patterns may be used.

The effect of the embossing of the pressure roll is to give areas of different compression which gives a texture to the surface, improves the flexibility, and gives excellent control to the permeation of blood.

As a surgical device, it is obviously desirable, almost mandatory, that the hemostatic felt be sterile at the time of use. The felt may be sterilized by an appropriate sterilizing cycle using ethylene oxide as a sterilizing agent. If ethylene oxide is used to sterilize, it is convenient that the ethylene oxide be diluted with carbon dioxide or a chlorofluoroalkane to such an extent that the sterilizing gas is non-explosive. Radiation sterilization or heat sterilization may be used, where equipment for such processes is available.

For storage stability, it is desirable that the felt hemostat be protected from atmospheric influences. Particularly, if the hemostatic felt contains hydrolyzable polyglycolic acid ester linkages, the linkages can be hydrolyzed by ambient moisture under room storage. Because the strength requirement for felt is comparativeley low, a certain degree of degradation is acceptable and because the long time strength requirement in tissue is very low, even if degraded to the point that the tissue absorbable fibers are absorbed in a comparatively short period of time, that is, under a few days, the surgical felt is still acceptable. It is desirable that such storage conditions be used so as to maintain the hemostatic felt in a dry environment so that whether used immediately after packaging or after a storage period of several years, the felt has the same characteristics and, hence, has known predictable attributes as far as the using surgeon is concerned.

A good method of sterilizing and storage is the same as is used for polyglycolic acid sutures on a commercial scale and as disclosed in U.S. Pat. No. 3,728,839, Arthur Glick, Apr. 24, 1973, STORAGE STABLE SURGICALLY ABSORBABLE POLYGLYCOLIC ACID PRODUCTS. As there described, the polyglycolic acid product is stored in a moisture proof envelope in which conveniently the product is packaged except for one open side and sterilized using ethylene oxide diluted so as to be non-explosive, and then while protecting sterility, the product is vacuum dried and the envelope sealed. By having the foil envelope hermetically sealed, as there taught, the hemostatic felt may be maintained in a usable form with consistent characteristics for a period of at least several years. Conveniently, but not necessarily, the felt may be placed between two sheets of paper, or a single sheet of paper with a fold, so that the felt is held in flat condition between the sheets during storage and service to the using surgeon.

For large sheets, the felt may be folded but for sheets up to 4 × 6 inches it is conveniently placed in an envelope large enough to hold the sheet flat. A plurality of sheets may be packaged in a single envelope if desired. Single sheets of about 4 × 6 inches are a surgically acceptable size, with the felt being cut to size by the surgeon, or an assistant, at the time of use. For many surgical procedures a single sheet is all that is required.

A double envelope, as described in U.S. Pat. No. 3,728,839, supra, is very convenient, and follows the techniques used in suture packages. The double envelope enables the sterile service of a sealed envelope, so that the surgeon or an assistant can open the inner envelope in a sterile area.

A single envelope such as shown in U.S. Pat. No. 3,017,990, Singerman, Jan. 23, 1962, STERILE PACKAGE FOR SURGICAL FABRIC, is also an economical and efficient package. The inner paper wrap maintains the sterility of the felt until used by the surgeon.

THE DRAWINGS

Figure 5:
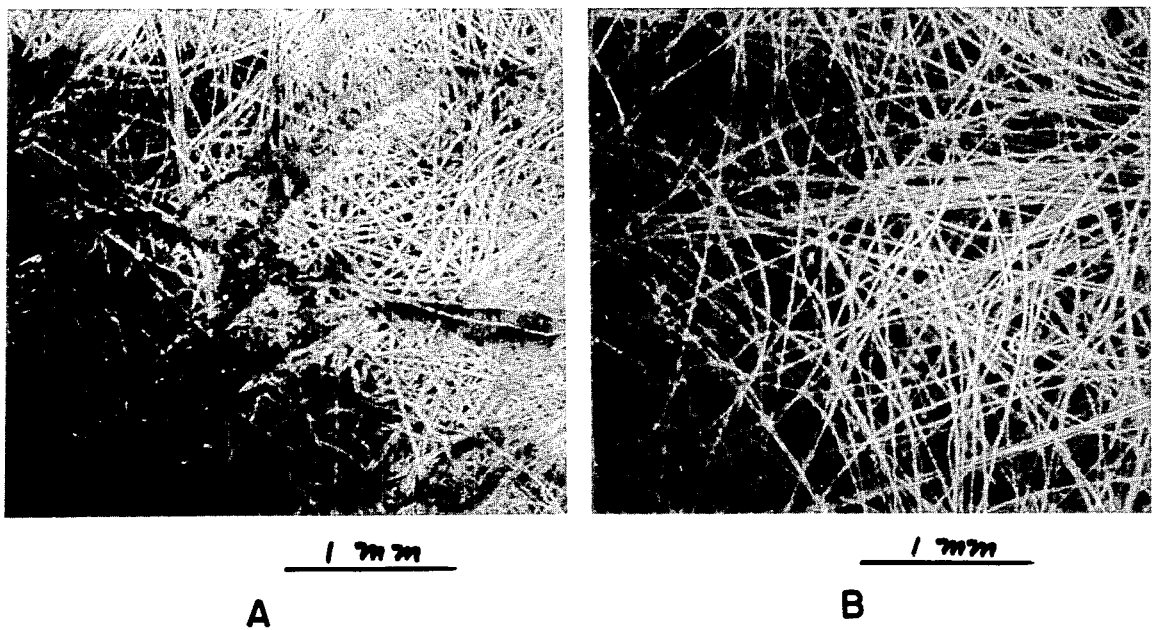

FIG. 5 is a composite scanning electron microscope photomicrograph at 30 diameters. The left side 5A shows the embossed felt. The right side 5B shows the air laid felt before embossing.

Figure 6:
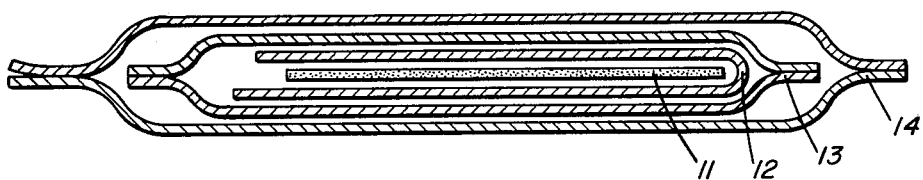

FIG. 6 is a drawing showing the embossed felt hemostat in a double envelope.

Figure 7:
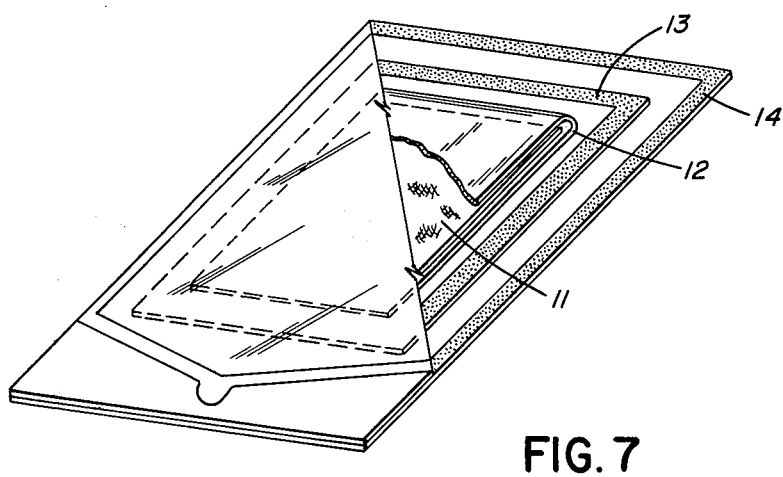

FIG. 7 is a drawing in pictorial, partly broken away showing the embossed felt hemostat in an envelope.

Figure 8:
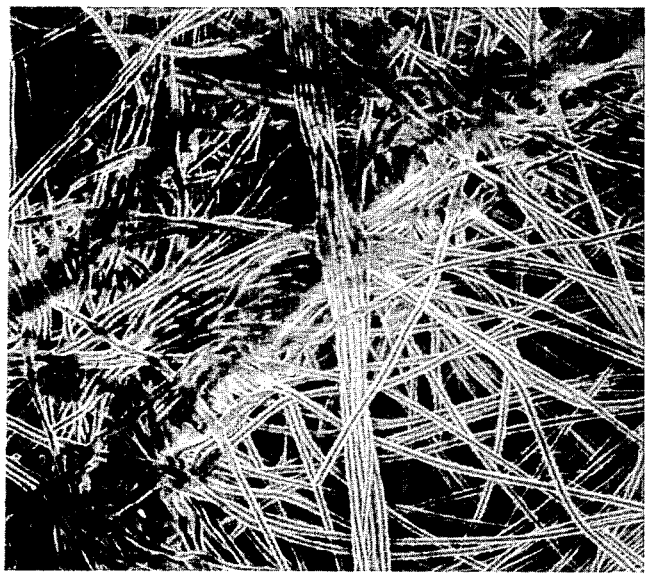

FIG. 8 is a scanning electron microscope photomicrograph at 100 diameters of the diamond embossed felt.

Figure 9:
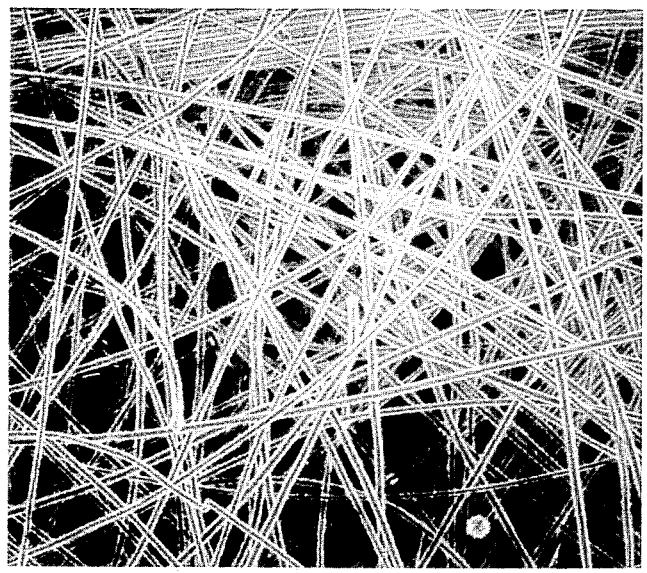

FIG. 9 is a scanning electron microscope photomicrograph at 100 diameters of an unembossed felt.

While the present invention is defined by the appended claims, it is illustrated by the following examples of specific constructions and usages of the present embossed surgical felt.

EXAMPLE 1

Polyglycolic acid having an inherent viscosity of about 1.05 was extruded into fibers of approximately 2 denier per filament using techniques described for the manufacturer of surgical sutures, supra. The continuous filaments are chopped into lengths of 1½ inches, fed into an air blast, suspended in air, and allowed to fall randomly onto a sheet of paper to a uniform density of 2.25 oz. per square yard. The felt was then run under an embossing roll with the embossing roll having an engraved figured pattern of diamonds with about a 3/32 inch spacing. The felt was compressed against a nylon backing roll, with the embossing roll being operated at a temperature of 345°–355°F., a pressure of 1,050 pounds per linear inch, and a speed of 15 feet per minute. After passing the free face of the felt under the embossing roll, the felt was turned over, the support paper removed, and the felt passed again under the embossing roll to emboss the second side.

FIGS. 1, 2, 5A, and 8 are of the thus heat embossed felt.

Figure 1:
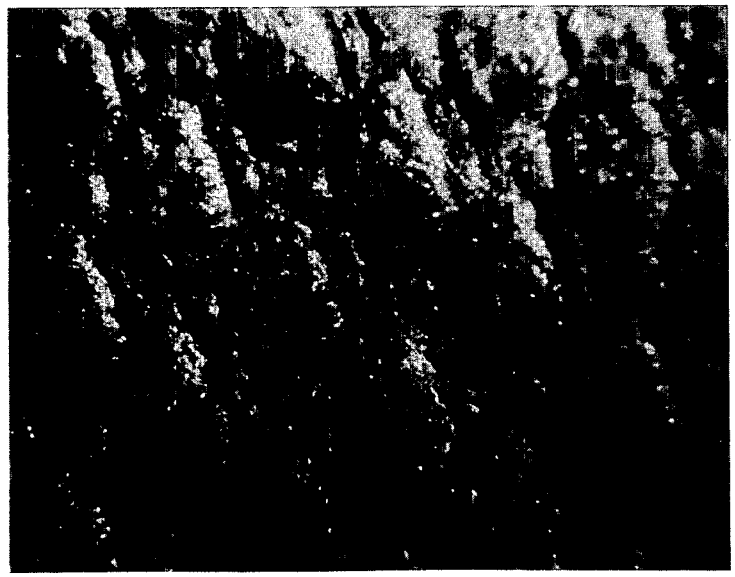
FIG. 1 shows a diamond embossing pattern at an optical magnification of about 10 diameters.
Figure 2:
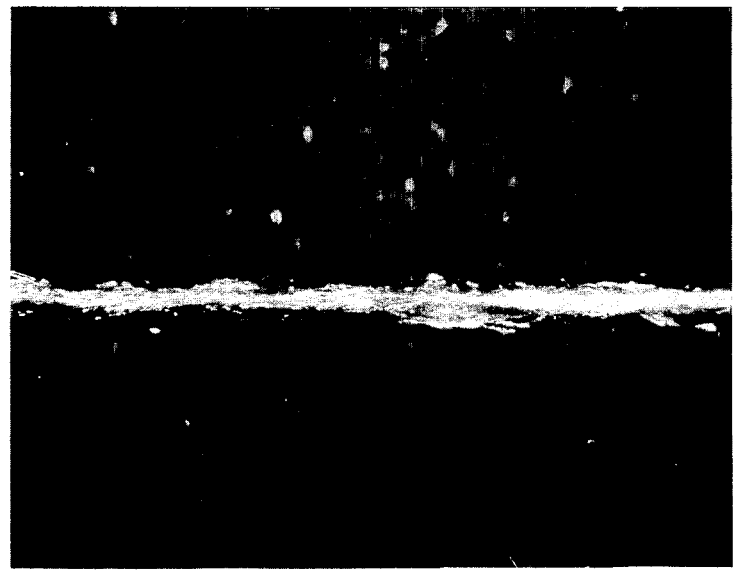
FIG. 2 shows a razor cut cross section of the embossed surgical felt of FIG. 1, at 10 diameters optical magnification.

FIG. 2 shows a cross section at a magnification of about 10 diameters.

FIGS. 5A and 5B show the felt for a hemostat before and after embossing. The figure at the right, 5B, is of the air laid web showing the individual fibers in random configuration as a comparatively thick soft felt. FIG. 5A shows the same felt which has been heat embossed which results in heating to incipient fusion and pressing together the felt along certain lines so that the individual fibers adhere to each other giving a compacted zone which aids in keeping the felt hemostat thin, aids in preventing the lateral transfer of liquids, and gives a desirable stiffness to the structure. The picture is at a magnification of 30 diameters and is taken with a scanning electron microscope which gives far greater depth of focus than an optical system. FIGS. 8 and 9 are similar photographs with an electron microscope showing the embossed and unembossed felt at about 100 diameters enlargement. The mashing together and fusion of the individual fibers can be seen in FIG. 8. FIG. 9 shows a random unoriented structure before the heat embossing. Before heat embossing, the fibers are springy and tend to stand up so that the felt has a soft fuzzy finish so that it is impractical to attempt to measure its thickness.

Figure 3:
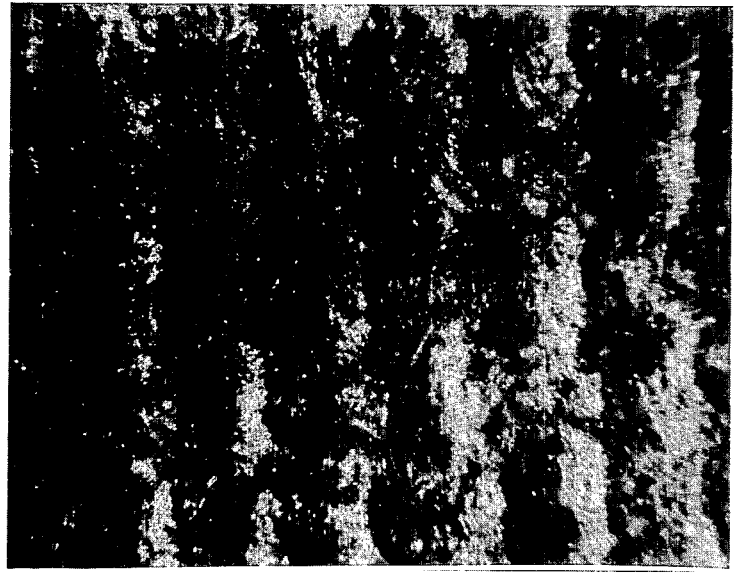
FIG. 3 shows an embossed surgical felt with a burlap pattern, at 10 diameters optical magnification.
Figure 4:
FIG. 4 shows the embossed surgical felt of FIG. 3 in a razor cut cross section, at 10 diameters optical magnification.

A similar section of the felt was run under the same speed and pressure conditions at the same temperature with an embossed roll having a burlap configuration. This gives to the surface of the felt the configuration resembling that of burlap. This is shown in FIGS. 3 for a face view and FIG. 4 for a cross section, at about 10 diameters.

Sections of the felt were cut to approximately 3 × 5 inches and placed in a sheet of glassine paper folded to enclose the embossed felt with a slight margin all around. The felt in the folded paper was placed in a slightly larger envelope of foil stock of the type as described in U.S. Pat. No. 3,728,839, supra, and the slightly open envelope, arranged to be sealed by parallel sealing clamps across the open face, was placed in an ethylene oxide oven, evacuated, 12% ethylene oxide in 88% dichlorodifluoromethane passed into the oven and allowed to stand for two hours, the oven was again evacuated, and held under vacuum until the ethylene oxide and any moisture was removed, and then the vacuum broken with dry nitrogen. Using precautions to preserve sterility, the envelope was then sealed across the open end, packaged in a larger strippable envelope, the inter envelope space sterilized and the thus doubly packaged absorbable surgical felt was storage stable and ready for use. As so packaged, the material will retain its characteristics for periods of at least several years and probably much longer. Tests conducted to date have not established the end of its useful life.

Such a package is shown in FIGS. 6 and 7 in which the hemostatic felt 11 is shown in a folded paper shield 12 with the paper shield extending slightly beyond the hemostatic felt on all sides and the paper shield in an inner moisture proof envelope 13. The inner moisture proof envelope in turn is sealed in a strippable outer envelope 14. The use of a paper shield in an outer envelope is shown in U.S. Pat. No. 3,017,990, Singerman, STERILE PACKAGE FOR SURGICAL FABRIC, Jan. 23, 1962. The sterilizing cycle and double envelope, including descriptions of materials of construction, for polyglycolic acid products, is set forth in detail in U.S. Pat. No. 3,728,839, supra.

EXAMPLE 2

A fast screening test for a hemostat is the rabbit "vena cava test" in which a slit approximately a quarter of an inch is formed longitudinally in the vena cava of a rabbit, the hemostat material placed over the opening and held by the finger of the surgeon for approximately 15 seconds, after which as the finger is removed, the hemostat is examined to see if it stops the flow of blood. The present hemostat with either the diamond or burlap embossing passes this test.

EXAMPLE 3

Stiffness and air porosity of hemostat

Using the procedure of Method of 5206 of Federal Test Method Standard 191, sections of embossed felt were tested by placing them on the test stand and extending out until the end of the specimen dropped to an angle of 41½°. The drape stiffness is reported as one-half the length of the overhang of the specimen when it reaches 41½° slope.

In the material of Example 1 this is found to be:

Diamond embossed:
   Horizontal (machine direction)     1.05 inches
   Vertical (perpendicular to machine direction)     1.15 inches
Burlap embossed:
   Horizontal     1.35 inches
   Vertical     1.83 inches
Unembossed web:
   Too fragile to be measured.

Similar tests were run following ASTM Method D-737-69 for air permeability. The results are reported as cubic feet per minute per square foot of fabric at 0.5 inch water pressure differential:

Diamond embossed:
   2.25 oz, per square yard, air permeability 133 cubic feet per minute per square foot of fabric at 0.5 inch water pressure differential.
Burlap embossed:
   2.25 oz. per square yard, air permeability 135 cubic feet per minute per square foot of fabric at 0.5 inch water pressure differential.
Unembossed web:
   2.25 oz. per square yard, air permeability 360 cubic feet per minute per square foot of fabric at 0.5 inch water pressure differential.

EXAMPLE 4

Hepatectomies

Sub-total hepatectomies were performed on a total of 15 randomly sexed New Zealand white rabbits weighing 2 to 3 kg. The operation was as follows:

The animals were anesthetized with sodium pentobarbital intravenously. The abdomen was shaved and a transverse incision made just posterior to the costal margin to expose the liver. The right medial, left medial, and left lateral liver lobes were identified, a Stockman penis clamp placed on each of two or three of the lobes as close to the hilum as possible, and the lobe excised distal to the clamp. The clamp was removed and bleeding proceeded until it stopped spontaneously or the animal expired. If the animal was alive when bleeding stopped, the laparotomy was repaired in the usual manner and the animal returned to its cage. The animal was protected with one ml. of penicillin and dihydrostreptomycin administered intro-muscularly as a prophylactic measure.

Similarly, groups of 10 rabbits of about the same weight and randomly sexed were tested using the polyglycolic acid hemostat of Example 1; an absorbable gelatin foam, an absorbable oxidized regenerated cellulose knit; and mattress sutures of 2/0 chromic surgical gut. Twenty to thirty percent of the liver was removed in each case and with the hemostats, the appropriate material was cut to a size slightly larger than the cut surface and secured with two or three stay sutures of 5/0 polyglycolic acid placed through the parenchyma about 5 mm. below the cut and tied with surgeons' knots on top of the material. The clamp was then removed. The surface area covered varied from animal to animal, but was about 12-13 square cm. For the suture group, two or three mattress sutures were placed parallel to the cut surface and knotted on the ventral surface of the lobe.

The laparotomy incisions were closed with 3/0 polyglycolic acid sutures in the standard manner and the animals returned to cages without further treatment.

RESULTS

Of the animals without hemostatic treatment, 73% died between 6 minutes and 12 hours after surgery.

Of the hemostats, the effectiveness was somewhat similar in all groups. After the clamp release, there was usually some minor oozing from around the edges for a short time. Seldom was there any leakage of blood through the material. The polyglycolic acid felt hemostat, on contact with the blood, became translucent but was otherwise unchanged in appearance and dimension. The gelatin foam became swollen as its interstices filled with blood. The oxidized regenerated cellulose turned black and acquired a gelatinous consistency.

The gelatin foam had to be pretreated by wetting the saline, squeezing out, rewetting and resqueezing, which is time consuming and the material is limp and pasty such that it sticks to instruments and gloves. The knitted oxidized regenerated cellulose shredded at the edges and also stuck to instruments and gloves. The mattress sutures were difficult to place tightly enough to stop bleeding without tearing through the liver capsule.

RESULTS

With the polyglycolic acid felt hemostat, there was no evidence of post-operative hemorrhage or unusual gross pathologic finding. Gross findings included minor focal infarction directly beneath the material and some of the hemostat was stained with bile but there was no evidence of peritoneal irritation due to bile leakage. At 15 days focal necrosis was largely resolved and the polyglycolic acid showed some absorption.

At 30 days very little of the polyglycolic acid felt hemostat was grossly identifiable and tissue response was unremarkable.

At 60 and 90 days the reaction was unremarkable except for a thin fibrous coating at the operative sites and regeneration of liver.

One animal in the group never recovered from anesthesia. There was no evidence of hemorrhage at the operative site.

Under similar conditions using the gelatin foam, at 3 days the implant was engorged with blood and bile and there was minor sub-implant infarction. The reaction at 7 days was similar but more diffuse.

At 15 days reaction was characterized by fibroplasis at the operative site, areas of focal necrosis, and bile cysts. The gelatin foam was largely intact.

The gelatin foam appeared to be absorbed by about 30 days although there were bile cysts in one of the animals and fiberplasia.

Sixty and 90 day reactions showed resolution of the above findings with liver regeneration. At 60 days, partially resorbed clots were found in the abdomen of one animal and bile cysts in the other. Two animals were found dead of pulmonary congestion and edema secondary to anesthesia overdose. No evidence of post-operative hemorrhage was noted.

OXIDIZED REGENERATED CELLULOSE

The three day findings included minor focal self-implant infarction and blood clot distal to the oxidized regenerated cellulose implant indicating post-operative bleeding through the material.

The seven day reaction was similar.

The findings for 15 days was similar to those of three and seven days. In addition, there was inflammatory exudate into some intra-hepatic spaces, fibroplasia and partially resorbed clots. The oxidized regenerated cellulose appeared to be about 50% absorbed. The findings at 30, 60, and 90 days were largely unremarkable, except for traces of the regenerated cellulose in the 60 and 90 day animals.

SUTURES AS HEMOSTATS

With the sutures, there was severe hepatic infarctions surrounding the mattress sutures at three days, and at seven days the findings were similar. At 15 through 90 days there was progressive resolution of the above responses. One animal was found dead on the fourth day from a technical error unrelated to the liver injury. Another was found dead on the first day with large clots on the liver and serosanguinous fluid throughout the abdomen.

It appears that although there were 73% deaths from the liver injury when untreated, when treated with the polyglycolic acid hemostatic felt, or the gelatin foam, or the regenerated oxide cellulose, there were no deaths attributable to hemorrhage. The embossed non-woven polyglycolic felt compared favorably with the conventional materials used for treatment. There appeared to be less post-operative bleeding using the embossed non-woven polyglycolic acid felt.

From the standpoint of performance in surgery, the embossed non-woven polyglycolic acid felt did not stick to instruments or gloves, maintained its integrity better, and could be handled, manipulated, and repositioned when wet without tearing or sticking to the instruments. The material was stiff enough that it could be sutured if desired, and used as a bolster.

EXAMPLE 5

Samples of the polyglycolic acid embossed hemostatic felt were tested in neuro-surgery on the brains of test animals. Small portions of the hemostatic felt were placed on the surfaces of the brain where hemorrhage was observed and held in place by the finger of the surgeon. A fine suction tube was used to remove blood which oozed through the hemostat or around the hemostat. After a short period, the flow of blood was effectively controlled with very little blood being absorbed in the hemostatic felt because it had been removed by suction. The flow of blood into and around the felt could be readily observed during the operating procedure. By contrast, when a gelatin foam is used for the same procedure, it is customary to hold it in place with a pad of cotton which prevents ready observation and interferes with removal of blood and introduces the possibility of cotton fibers being trapped within the wound. On closing the embossed non-woven polyglycolic acid felt hemostat within the wound, there appeared to be minimal risk of hemorrhage and recovery was uneventful. Autopsy showed no hemorrhage and rapid absorption of the polyglycolic acid felt within the animal and a minimal of interference with the healing of the wound.

In humans, where the brain or other neural tissue was damaged, the present embossed polyglycolic acid surgical felts are found to give good hemostasis and permit regeneration at least as rapidly as more conventional surgical procedures.

The denier per filament, the thickness of the felt sponge, its stiffness, and handling characteristics can be varied by using different size filaments, different lengths of filaments and different temperatures and pressure during the embossing operation to present felts with a thickness and stiffness which is preferred by a surgeon in connection with a specific operating procedure. As different surgeons have different preferences and there is a wide variation of surgical procedures in which hemostasis is desired, a range of thicknesses and stiffnesses may be provided.

Usually, the sponge of Example 1 is sufficiently versatile to cover most operative procedures and most surgeons' preferences and, hence, permits effective wide range hemostasis with a minimum of inventory and supply problems.

I claim:

1. A hemostatic surgical felt comprising a sterile felt of fibers of 0.5 to 12 denier and ¼ inch to 3 inch length of a tissue absorbable polymer subject to hydrolytic degradation to non-toxic tissue compatible absorbable components, and which polymer has glycolic acid ester linkages, which felt has a weight of 0.5 ounce to 12 ounces per square yard and textured and partially compressed heat embossed surfaces, whereby the rate of penetration of blood is reduced, and the adhesion to bleeding surfaces enhanced, and which is completely absorbed when enclosed in a living tissue.

2. The hemostatic felt of claim 1 in which the tissue absorbable polymer is polyglycolic acid.

3. A method of protecting the exposed wound surfaces of an internal organ of a living mammal which comprises covering said wound surface with a sterile hemostatic surgical felt of fibers of 0.5 to 12 denier and ¼ inch to 3 inch length of a tissue absorbable polymer subject to hydrolytic degradation to non-toxic tissue compatible absorbable components, and which polymer has glycolic acid ester linkages, which felt has a weight of 0.5 ounce to 12 ounces per square yard and textured and partially compressed heat embossed surfaces, whereby the rate of penetration of blood is reduced, and the adhesion to bleeding surfaces enhanced, and which is completely absorbed when enclosed in living tissue, attaching the said felt to said organ, closing the said organ into said living mammal, and during the healing process, absorbing said felt into the body tissues of said mammal.

4. The method of claim 3 in which the internal organ is the liver.

5. The method of claim 3 in which the internal organ is of neural tissue.

6. The method of claim 5 in which the internal organ is the brain.

7. A hemostatic surgical felt comprising a sterile felt of air laid fibers of a tissue absorbable polymer of glycolic acid of 0.5 to 12 denier and ¼ inch to 3 inch length which felt has textured and partially compressed heat embossed surfaces, a weight of about 2.25 ounces per square yard, a stiffness of 1.05 to 1.83 inches, measured as one half the length of the overhang of a specimen on a flat horizontal surface which drops to an angle of 41½° and which before embossing is too fragile for stiffness measurement, and an air permeability of about 135 cubic feet per minute per square foot at 0.5 inches of water pressure differential, and which before embossing has an air permeability of about 360 cubic feet per minute per square foot at 0.5 inches of water pressure differential whereby the rate of penetration of blood is reduced, and the adhesion to bleeding surfaces enhanced, and which is completely absorbed when enclosed in living tissue.

8. A method of protecting the exposed wound surfaces of an internal organ of a living mammal which comprises covering said wound surface with a sterile hemostatic surgical felt of air laid fibers of a tissue absorbable polymer of glycolic acid of 0.5 to 12 denier and a ¼ inch to 3 inch length which felt has textured and partially compressed heat embossed surfaces, a weight of about 2.25 ounces per square yard, a stiffness of 1.05 to 1.83 inches, measured as one half the length of the overhang of a specimen on a flat horizontal surface which drops to an angle of 41½° and which before embossing is too fragile for stiffness measurement, and an air permeability of about 135 cubic feet per minute per square foot at 0.5 inches of water pressure differential, and which before embossing has an air permeability of about 360 cubic feet per minute per square foot at 0.5 inches of water pressure differential, whereby the rate of penetration of blood is reduced, and the adhesion to bleeding surfaces enhanced, and which is completely absorbed when enclosed in living tissue, attaching the said felt to said organ, closing the said organ into said living mammal, and during the healing process, absorbing said felt into the body tissues of said mammal.

* * * * *